United States Patent [19]

Sayo et al.

[11] Patent Number: 4,916,252

[45] Date of Patent: Apr. 10, 1990

[54] PROCESS FOR PREPARING OPTICALLY ACTIVE ALCOHOL

[75] Inventors: Noboru Sayo; Takao Saito; Hidenori Kumobayashi; Susumu Akutagawa, all of Kanagawa; Ryoji Noyori; Hidemasa Takaya, both of Aichi, all of Japan

[73] Assignee: Takasago International Corporation, Tokyo, Japan

[21] Appl. No.: 207,428

[22] Filed: Jun. 16, 1988

[30] Foreign Application Priority Data

Jun. 18, 1987 [JP] Japan ................. 62-150187

[51] Int. Cl.$^4$ ............................................. C07C 101/30
[52] U.S. Cl. ........................................ 560/39; 560/60; 560/122; 560/126; 560/169; 560/170; 560/180; 560/184; 560/186; 564/346; 564/358; 564/453; 564/507; 568/660; 568/662; 568/807; 568/811; 568/821; 568/823; 568/833; 568/834; 568/838; 568/842; 568/846; 568/862
[58] Field of Search ............... 560/186, 39, 60, 122, 560/126, 169, 170, 180, 184; 564/358, 346, 453, 507; 568/660, 662, 807, 811, 821, 823, 833, 834, 838, 842, 846, 862

[56] References Cited

U.S. PATENT DOCUMENTS 3,883,580  5/1975  Solodar ..................... 564/358

FOREIGN PATENT DOCUMENTS 0174057  3/1986  European Pat. Off. .

OTHER PUBLICATIONS

Bianchi et al., *J. Organometallic Chem.*, vol. 198, pp. 73–80 (1980).
Noyori et al., *J. Am. Chem. Soc.*, vol. 186, pp. 7117–7119 (1986).
Takaya et al., *J. Am. Chem. Soc.*, vol. 109, pp. 1596–1597.
Chemistry Letters–A. Tai et al., pp. 1049–1050 (1979).
J. Chem. Soc., Chem. Commun.–T. Ikariya et al.–pp. 922–924 (1985).

*Primary Examiner*—Bruce D. Gray
*Attorney, Agent, or Firm*—Sughrue, Mion, Zinn, Macpeak & Seas

[57] ABSTRACT

A process for preparing an optically active alcohol is disclosed, which comprises asymmetrically hydrogenating a 1,3-diketone in the presence of a ruthenium-optically active phosphine complex as a catalyst. The resulting alcohol has high optical purity.

3 Claims, No Drawings

PROCESS FOR PREPARING OPTICALLY ACTIVE ALCOHOL

FIELD OF THE INVENTION

This invention relates to a process for preparing an optically active alcohol useful as an intermediate for synthesizing pharmaceuticals, an important assistant for obtaining optically active compounds, a liquid crystal material, and the like by asymmetric hydrogenation of 1,3-diketones in the presence of a ruthenium-optically active phosphine complex as a catalyst.

BACKGROUND OF THE INVENTION

Known techniques for asymmetrically synthesizing optically active alcohols include a process comprising asymetric hydrogenation using baker's yeast and a process comprising asymetric hydrogenation using a specific catalyst.

In particular, with respect to asymmetric hydrogenation of β-diketones to obtain optically active alcohols, it has been reported that the asymmetric hydrogenation can be carried out by using a tartaric acid-modified nickel catalyst. According to this technique, asymmetric hydrogenation of acetylacetone gives 2,4-pentanediol in an optical yield of 87% ee as disclosed in A. Tai et al., *Chem. Lett.*, 1049–1050 (1979).

Although the process using baker's yeast produces an alcohol having relatively high optical purity, the resulting optically active alcohol is limited in absolute configuration, and synthesis of an enantiomer is difficult.

The process using a tartaric acid-modified Raney nickel catalyst involves disadvantages of difficulty in preparing the catalyst and insufficient optical yield.

SUMMARY OF THE INVENTION

As a result of extensive investigations with the purpose of settling the above-described problems, the inventors have found that an optically active alcohol having high optical purity can be obtained by asymmetric hydrogenation of a 1,3-diketone in the presence of a relatively cheap ruthenium-optically active phosphine complex as a catalyst. The present invention has been completed based on this finding.

The present invention relates to a process for preparing an optically active alcohol represented by formula (I):

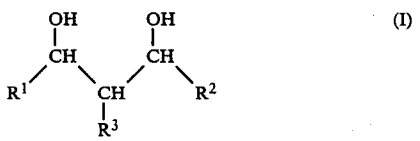

wherein $R^1$ and $R^2$ each represents an alkyl group having from 1 to 8 carbon atoms, a haloalkyl group (the alkyl moiety thereof preferably has from 1 to 4 carbon atoms), a hydroxyalkyl group (the alkyl moiety thereof preferably has from 1 to 4 carbon atoms), a trifluoromethyl group, a substituted or unsubstituted phenyl-substituted lower alkyl group (the alkyl moiety thereof preferably has from 1 to 4 carbon atoms; and examples of the, substituent include a halogen atom, a hydroxyl group, and a lower include halogen a tom, a hydroxyl group, and a lower alkoxy group having preferably from 1 to 4 carbon atoms), an alkoxycarbonyl-substituted lower alkyl group (the alkyl moiety thereof preferably has from 1 to 4 carbon atoms), a lower aminoalkyl group (the alkyl moiety thereof preferably has from 1 to 4 carbon atoms), a lower alkyl-substituted aminoalkyl group (the alkyl moiety thereof preferably has from 1 to 4 carbon atoms), a substituted or unsubstituted phenyl group (examples of the substituent include a halogen atom, a hydroxyl group, and a lower alkoxy group having preferably from 1 to 4 carbon atoms), or a benzyloxy group; $R^3$ represents a hydrogen atom, a halogen atom, a lower alkyl group (the alkyl moiety thereof preferably has from 1 to 4 carbon atoms), or a lower alkoxycarbonyl group (the alkyl moiety thereof preferably has from 1 to 4 carbon atoms); or $R^1$ and $R^2$, or $R^2$ and $R^3$ are taken together with the carbon atoms therebetween to from a 5- to 7-membered ring which may contain a lower alkoxycarbonyl group (the alkyl moiety thereof preferably has from 1 to 4 carbon atoms) or a double bond, which comprises asymmetrically hydrogenating a 1,3-diketone represented by formula (II):

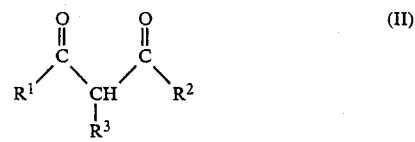

wherein $R^1$, $R^2$, and $R^3$ are as defined above, in the presence of a ruthenium-optically active phosphine complex as a catalyst.

DETAILED DESCRIPTION OF THE INVENTION

The 1,3-diketone represented by formula (II) which can be used in the present invention as a starting compound specifically includes acetylacetone, 3,5-heptanedione, 4,6-nonanedione, 5,7-undecadione, 1,3-diphenyl-1,3-propanedione, 1,5-diphenyl-2,4-pentanedione, 1,3-di(trifluoromethyl)-1,3-propanedione, 1,5-dichloro-2,4-pentanedione, 1,5-dihydroxy-2,4-pentanedione, 1,5-dibenzyloxy-2,4-pentanedione, 1,5-diamino-2,4-pentanedione, 1,5- di(methylamino)-2,4-pentanedione, 1,5-di(dimethylamino)-2,4-pentanedione, 1-phenyl-1,3-butanedione, 1-phenyl-1,3-pentanedione, 1-phenyl-1,3-hexanedione, 1-phenyl-1,3-heptanedione, 2,4-hexanedione, 2,4-heptanedione, 2,4-octanedione, 2,4-nonanedione, 3,5-nonanedione, 3,5-decanedione, 2,4-dodecanedione, 3-methyl-2,4-pentanedione, 3-chloro-2,4-pentanedione, 3-carbomethoxy-2,4-pentanedione, 3-carboethoxy-2,4-pentanedione, 1,3-cyclopentanedione, 1,3-cyclohexanedione, 1,3-cycloheptanedione, 5-carboethoxy-1,3-cyclopentanedione, 4-cyclopenten-1,3-dione, 2-acetyl- 1-cyclopentanone, 2-acetyl-1-cyclohexanone, methyl 3,5-dioxo-hexanoate, etc.

The ruthenium-optically active phosphine complex to be used as a catalyst includes those represented by the following formulae (III) and (V):

wherein $R^4$-BINAP represents a tertiary phosphine represented by formula (IV):

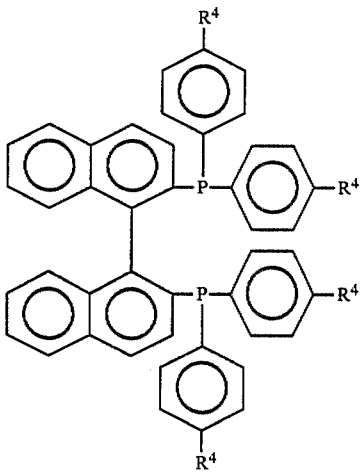

(IV)

wherein $R^4$ represents a hydrogen atom, a methyl group, or a t-butyl group; S represents a tertiary amine; when y represents 0, then x represents 2, z represents 4, and p represents 1; and when y represents 1, then x represents 1, z represents 1, and p represents 0.

$$[RuH_l(R^4\text{-BINAP})_v]Y_w \quad (V)$$

wherein $R^4$-BINAP is as defined above; Y represents $ClO_4$, $BF_4$, or $PF_6$; when l represents 0, v represents 1, and w represents 2; and when l represents 1, then v represents 2, and w represents 1.

In formulae (III) and (V), "BINAP" represents a 2,2-bis(diphenylphosphino)-1,1'-binaphthyl moiety (hereinafter the same).

The compound of formula (III) can be obtained by the process disclosed in T. Ikariya et al., *J. Chem. Soc., Chem. Commun.*, 922-924 (1985) and Japanese Patent Application (OPI) No. 63690/86 (the term "OPI" as used herein means "unexamined published Japanese patent application"). More specifically, the complex of formula (III) wherein y is 0 can be prepared by reacting 1 mol of $[RuCl_2(COD)]_n$ (wherein COD represents cycloocta-1,5-diene, hereinafter the same), which is obtained by reacting ruthenium chloride and COD in an ethanol solution, and 1.2 mols of a 2,2'-bis(di-p-$R^4$-phenylphosphino)-1,1'-binaphthyl ($R^4$-BINAP) under heating in a solvent, e.g., toluene, ethanol, etc., in the presence of 4 mols of a tertiary amine, e.g., triethylamine. The complex of formula (III) wherein y is 1 can be obtained by reacting 1 mol of $[RuCl_2(COD)]_n$, 2.25 mols of $R^4$-BINAP, and 4.5 mols of a tertiary amine.

The complex of formula (V) wherein l is 0, v is 1, and w is 2 can be prepared by reacting $Ru_2Cl_4(R^4BINAP)_2$-$(NEt_3)$ (wherein Et represents an ethyl group, hereinafter the same), which is obtained by the above-described process, with a salt represented by formula (VI):

$$MY \quad (VI)$$

wherein M represents Na, K, Li, Mg, or Ag; and Y is as defined above, in a solvent system comprising water and methylene chloride in the presence of a quaternary ammonium salt or quaternary phosphonium salt represented by formula (VII):

$$R^5R^6R^7R^8AB \quad (VII)$$

wherein $R^5$, $R^6$, $R^7$, and $R^8$ each represents an alkyl group having from 1 to 16 carbon atoms, a phenyl group, or a benzyl group; A represents a nitrogen atom or a phosphorus atom; and B represents a halogen atom, as a phase transfer catalyst. The reaction can be carried out by adding the reactants and the phase transfer catalyst of formula (VII) to a mixed solvent of water and methylene chloride and stirring the system. The amounts of the salt of formula (VI) and of the phase transfer catalyst of formula (VII) to be added range from 2 to 10 mols (preferably 5 mols) and from 1/100 to 1/10 mol, respectively, per mol of ruthenium. The reaction sufficiently proceeds by stirring at a temperature of from 5° to 30° C. for a period of from 6 to 18 hours, and usually 12 hours. Examples of the phase transfer catalyst of formula (VII) are described in literatures, e.g., W. P. Weber and G. W. Gokel, Sokan Ido Shokubai (Japanese translation), 1st Ed., Kagaku Dojinsha (1978). After completion of the reaction, the reaction mixture is allowed to stand still, followed by liquid separation. After the aqueous layer is removed, the methylene chloride solution is washed with water, and methylene chloride is removed by distillation under reduced pressure to obtain the desired compound.

The complex of formula (V) wherein l is 1, v is 2, and w is 1 can be prepared by reacting $RuHCl(R^4\text{-BINAP})_2$ obtainable by the process disclosed in Japanese Patent Application (OPI) No. 63690/86 with the salt of formula (VI) in a mixed solvent of water and an organic solvent, e.g., methylene chloride, in the presence of the phase transfer catalyst of formula (VII). The amounts of the salt of formula (VI) and of the phase transfer catalyst of formula (VII) range from 2 to 10 mols (preferably 5 mols) and from 1/100 to 1/10 mol, respectively, per mol of ruthenium. This reaction sufficiently proceeds by stirring at a temperature of from 5° to 30° C. for a period of from 6 to 18 hours, and usually 12 hours.

Specific examples of the above-described ruthenium-phosphine complex according to the present invention are shown below.

$Ru_2Cl_4(BINAP)_2(NEt_3)$ $Ru_2Cl_4(T\text{-BINAP})_2(NEt_3)$

[T-BINAP represents 2,2'-bis(di-p-tolylphosphino) -1,1'-binaphthyl]

$Ru_2Cl_4(t\text{-Bu-BINAP})_2(NEt_3)$

[t-Bu-BINAP represents 2,2'-bis(di-p-t-butylphenylphosphino) 1,1'-binaphthyl]

$RuHCl[BINAP]_2$ $RuHCl[T\text{-BINAP}]_2$ $RuHCl[t\text{-Bu-BINAP}]_2$ $[Ru(BINAP)](ClO_4)_2$ $[Ru(T\text{-BINAP})](ClO_4)_2$ $[Ru(t\text{-Bu-BINAP})](ClO_4)_2$ $[Ru(BINAP)](BF_4)_2$ $[Ru(T\text{-BINAP})](BF_4)_2$ $[Ru(t\text{-Bu-BINAP})](BF_4)_2$ $[Ru(BINAP)](PF_6)_2$ $[Ru(T\text{-BINAP})](PF_6)_2$ $[RuH(BINAP)_2]ClO_4$ $[RuH(T\text{-BINAP})_2]ClO_4$ $[RuH(BINAP)_2]BF_4$ $[RuH(T\text{-BINAP})_2]BF_4$ $[RuH(BINAP)_2]PF_6$ $[RuH(T\text{-BINAP})_2]PF_6$ In carrying out the present invention, a 1,3-diketone of formula (II) is dissolved in an amphiprotic solvent, e.g., methanol, ethanol, methyl cellosolve, etc., or a mixed solvent of such an amphiprotic solvent with tetrahydrofuran, toluene, benzene, methylene chloride, etc. The solution is charged in an autoclave, and from 1/100 to 1/50,000 mol of a ruthenium-optically active phosphine complex is added thereto per mol of the 1,3-diketone. The hydrogenation reaction is effected under stirring at a temperature of from 5° to 50° C., and preferably from 25° to 35° C., at a hydrogen pressure of from 5 to 100 kg/cm$^2$ for a period of from 1 to 48 hours. After completion of the reaction, the solvent is removed by distillation, and the residue is distilled under reduced pressure or subjected to silica gel column chromatography to thereby isolate the desired optically active alcohol of formula (I) in a substantially quantitative yield.

The present invention will now be illustrated in greater detail with reference to Reference Examples and Examples, but it should be understood that the present invention is not deemed to be limited thereto. In these examples, analytical instruments and conditions used for various analyses are as follows.

(1) Gas Chromatography (GC): SHIMADZU GC-9A, manufactured by Shimadzu Corporation
  Column: PEG-20M Silica Capillary, 0.25 mm in diameter and 25 m in length, manufactured by Gasukuro Kogyo Inc.
  Measurement Temperature: 100°–250° C. and increasing at a rate of
  3° C./min.

(2) High Performance Liquid Chromatography (HPLC): Hitachi Liquid Chromatography-655A-11 manufactured by Hitachi, Ltd.
  Column: Chemcopack Nucleosil 100-3, 4.6 mm in diameter and 300 mm in length, manufactured by Chemco Co.
  Developing Solvent: Hexane:diethyl ether=7:3; flow rate: 1 ml/min
  Detector: UV Detector 655A (UV-254), manufactured by Hitachi, Ltd.

(3) Optical Rotation: Polarimeter DIP-4, manufactured by Nippon Bunko Kogyo K.K.

(4) $^{31}$P NMR Spectrum: JNM-GX400 (161 MHz) manufactured by JEOL Ltd. Chemical shift was determined by using 85% phosphoric acid as an external standard.

REFERENCE EXAMPLE 1

Synthesis of Ru$_2$Cl$_4$((+) -BINAP)$_2$(NEt$_3$) (di[2,2'-bis(-diphenylphosphino) -1,1'-binaphthyl]tetrachloro-diruthenium triethylamine):

To 100 ml of toluene were added 1 g (3.56 mmols) of [RuCl$_2$(COD)]$_n$, 2.66 g (4.27 mmols) of (+)-BINAP, and 1.5 g of triethylamine in a nitrogen atmosphere, and the mixture was heat-refluxed for 10 hours. The solvent was removed from the reaction mixture by distillation under reduced pressure, and the residual solid was dissolved in methylene chloride, followed by filtration through Celite. The filtrate was concentrated to dryness to obtain 3.7 g of the entitled compound as a deep brown solid.

Elemental Analysis for C$_{94}$H$_{79}$Cl$_4$NP$_4$Ru$_2$: Calcd. (%): Ru 11.96; C 66.85; H 4.71; P 7.33. Found (%): Ru 11.68; C 67.62; H 4.97; P 6.94.

$^{31}$P NMR (CDCl$_3$) δppm: 51.06 (s), 51.98 (s), 53.87 (s), and 54.83 (s).

REFERENCE EXAMPLE 2

Synthesis of [Ru((−)-T-BINAP)](ClO$_4$)$_2$ ([2,2'-bis(di-p-tolylphosphino)-1,1'-binaphthyl]ruthenium perchlorate):

In a 250 ml-volume Schlenk's tube was charged 0.54 g (0.3 mmol) of Ru$_2$Cl$_4$((−)-T-BINAP)$_2$(NEt$_3$). After thorough displacement of the atmosphere with nitrogen gas, 60 ml of methylene chloride was added thereto, and then a solution of 0.73 g (6.0 mmols) of sodium perchlorate in 60 ml of water and a solution of 16 mg (0.06 mmol) of triethylbenzylammonium bromide in 3 ml of water were added to the mixture. The mixture was stirred at room temperature for 12 hours. After completion of the reaction, the reaction mixture was allowed to stand, and the aqueous layer was removed. The methylene chloride was removed from the organic layer by distillation under reduced pressure, and the residue was dried under reduced pressure to obtain 0.59 g (yield: 99.6%) of the entitled compound as a deep brown solid.

Elemental Analysis for C$_{48}$H$_{40}$Cl$_2$O$_8$P$_2$Ru: Calcd. (%): Ru 10.32; C 58.90; H 4.12; P 6.33. Found (%): Ru 10.08; C 58.61; H 4.53; P 5.97.

$^{31}$P NMR (CDCl$_3$) δppm: 12.920 (d, J=41.1 Hz) and 61.402 (d, J=41.1 Hz).

EXAMPLE 1

Synthesis of (2R, 4R)-(−)-2,4-Pentanediol

In a 200 ml-volume stainless steel-made autoclave whose atmosphere had been replaced with nitrogen were charged 11.4 ml (110 mmols) of acetylacetone and 50 ml of methanol, and 93 mg (0.055 mmol) of Ru$_2$Cl$_4$((+)BINAP)$_2$(NEt$_3$) as prepared in Reference Example 1 was added thereto to effect hydrogenation at a temperature of 30° C. under a hydrogen pressure of 40 kg/cm$^2$ for 20 hours. The solvent was removed by distillation, and the residue was distilled under reduced pressure to obtain 11.2 g (yield: 98%) of the entitled compound having a boiling point of 98° to 100° C./10 mmHg.

The product was found to have a purity of 99.4% by GC and an optical rotation $[\alpha]_D^{20}$ of +39.57° C. (C=2.25 CHCl$_3$).

The resulting alcohol was esterified with (+)-α-methoxy-α-trifluromethylphenylacetyl chloride, and the ester was analyzed by GC and HPLC. The results revealed that the product was a mixture comprising 99% of (2R, 4R)-(−)-2,4-pentanediol and 1% of (2RS, 4RS)-(±)-2,4-pentanediol. That is, the ratio of the anti form to the syn form was 99:1, and the optical yield of the (2R, 4R)-(−)-2,4pentanediol was thus found to be 98% ee.

EXAMPLES 2 TO 13

The same procedure of Example 1 was repeated, except for altering the reaction substrate, catalyst and reaction conditions as shown in Table 1 below. The analytical results are also shown in Table 1.

TABLE 1

| Example No. | Substrate R¹ | Substrate R² | Substrate R³ | Catalyst | Substrate/Catalyst (mol/mol) | Reaction Condition Hydrogen Pressure (kg/cm²) | Reaction Condition Temperature (°C) | Time (hr) | Product | Results of Reaction* anti:syn | Results of Reaction* Optical Yield (% ee) | Yield (%) |
|---|---|---|---|---|---|---|---|---|---|---|---|---|
| 2 | C₆H₅ | C₆H₅ | H | Ru₂Cl₄((+)-BINAP)₂(NEt₃) | 1000 | 40 | 30 | 30 | OH OH / Ph-CH-CH-CH-CH-Ph | 90:10 | 99 | 89 |
| 3 | CH₃ | C₆H₅ | H | Ru₂Cl₄((−)-BINAP)₂(NEt₃) | 1000 | 40 | 30 | 24 | OH OH / CH₃-CH-CH-Ph | 93:7 | 94(54) | 98 |
| 4 | CH₃ | CH₃ | CH₃ | [Ru((+)-BINAP)](ClO₄)₂ | 1000 | 40 | 30 | 20 | OH OH / isopropyl-CH-CH-CH₃ | 95:5 | 99 | 92 |
| 5 | CH₃ | CH₂CO₂CH₃ | H | [Ru((+)-T-BINAP)](BF₄)₂ | 1000 | 40 | 30 | 22 | OH OH / CH₃-CH-CH-CH₂-CO₂CH₃ | 63:37 | 95(99) | 78 |
| 6 | CF₃ | CF₃ | H | [Ru((−)-T-BINAP)](PF₆)₂ | 500 | 40 | 30 | 44 | OH OH / CF₃-CH-CH-CF₃ | 85:15 | 78 | 89 |
| 7 | CH₃ | CH₃ | Cl | [RuH((−)-BINAP)₂]ClO₄ | 500 | 40 | 30 | 32 | OH OH / CH₃-CH-CCl-CH₃ | 98:2 | 98 | 93 |
| 8 | CH₃ | CH₃ | CO₂C₂H₅ | Ru₂Cl₄((−)-BINAP)₂(NEt₃) | 1000 | 40 | 30 | 20 | OH OH / CH₃-CH-C(CO₂C₂H₅)-CH-CH₃ | 100:0 | 99 | 89 |
| 9 | CH₂Cl | CH₂Cl | H | [RuH((+)-T-BINAP)₂]BF₄ | 1000 | 40 | 30 | 24 | OH OH / ClCH₂-CH-CH-CH₂Cl | 90:10 | 87 | 94 |
| 10 | CH₂N(CH₃)₂ | CH₂N(CH₃)₂ | H | [Ru((+)-T-BINAP)](ClO₄)₂ | 1000 | 40 | 30 | 20 | OH OH / (CH₃)₂NCH₂-CH-CH-CH₂N(CH₃)₂ | 85:15 | 91 | 85 |
| 11 | OCH₂-C₆H₅-OCH₂- | OCH₂-C₆H₅-OCH₂- | H | [Ru((−)-BINAP)](BF₄)₂ | 1000 | 40 | 30 | 22 | OH OH / PhCH₂O-CH₂-CH-CH-CH₂-OCH₂Ph | 91:9 | 93 | 97 |

TABLE 1-continued

| | Substrate $R^1-\overset{O}{\overset{\|}{C}}-\overset{R^3}{\overset{\|}{CH}}-\overset{O}{\overset{\|}{C}}-R^2$ | | | Reaction Condition | | | | | Results of Reaction | | |
|---|---|---|---|---|---|---|---|---|---|---|---|
| Example No. | $R^1$ | $R^2$ | $R^3$ | Catalyst | Substrate/ Catalyst (mol/mol) | Hydrogen Pressure (kg/cm$^2$) | Temperature (°C.) | Time (hr) | Product | anti:syn | Optical Yield* (% ee) | Yield (%) |
| 12 | —CH$_2$CH$_2$— | | H | Ru$_2$Cl$_4$((+)-BINAP)$_2$(NEt$_3$) | 1000 | 40 | 30 | 24 | HO―⬠―OH | 95:5 | 97 | 90 |
| 13 | C$_4$H$_9$ | CH$_3$ | H | Ru$_2$Cl$_4$((−)-T-BINAP)$_2$(NEt$_3$) | 1000 | 40 | 30 | 20 | (OH OH structure) | 97:3 | 99 | 97 |

*The numeral value in the parenthesis means an optical yield of the smaller amount component.

As described above, the present invention provides an industrially valuable process for preparing a useful optically active alcohol at high efficiency by asymmetric hydrogenation of 1,3-diketones.

While the invention has been described in detail and with reference to specific embodiments thereof, it will be apparent to one skilled in the art that various changes and modifications can be made therein without departing from the spirit and scope thereof.

What is claimed is:

1. A process for preparing an optically active alcohol represented by formula (I):

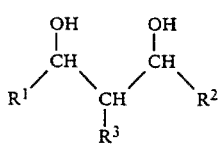
(I)

wherein $R^1$ and $R^2$ each represents an alkyl group having from 1 to 8 carbon atoms, a haloalkyl group, a hydroxyalkyl group, a trifluoromethyl group, a phenyl-substituted lower alkyl group, an alkoxycarbonyl-substituted lower alkyl group, a lower aminoalkyl group, a lower alkyl-substituted lower aminoalkyl group, a phenyl group, or a benzyloxy group; $R^3$ represents a hydrogen atom, a halogen atom, a lower alkyl group, or a lower alkoxycarbonyl group; or $R^1$ and $R^2$, or $R^2$ and $R^3$ are taken together with the carbon atoms therebetween to form a 5- to 7-membered ring which may contain a lower alkoxycarbonyl group or a double bond, which comprises asymmetrically hydrogenating a $\frac{1}{3}$-diketone represented by formula (II):

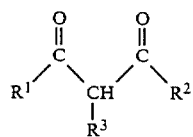
(II)

wherein $R^1$, $R^2$, and $R^3$ are as defined above, in the presence of a ruthenium-optically active phosphine complex as a catalyst, wherein said ruthenium-optically active phosphine complex is a compound represented by formula (III):

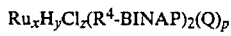

$$Ru_xH_yCl_z(R^4\text{-BINAP})_2(Q)_p \qquad (III)$$

wherein $R^4$-BINAP represents a tertiary phosphine represented by formula (IV):

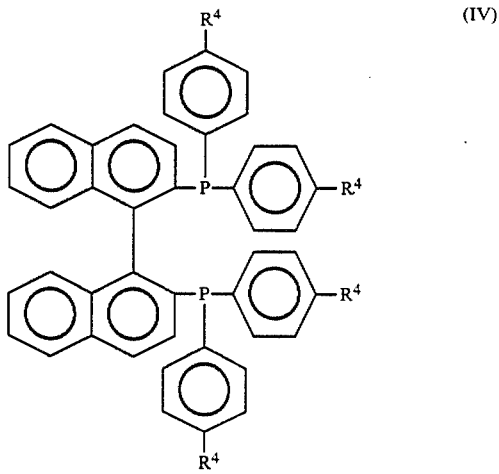
(IV)

wherein $R^4$ represents a hydrogen atom, a methyl group, or a t-butyl group; Q represents a tertiary amine; when y represents 0, then x represents 2, z represents 4, and p represents 1; and when y represents 1, then x represents 1, z represents 1, and p represents 0, or a compound represented by formula (v):

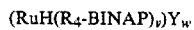

$$(RuH(R_4\text{-BINAP})_v)Y_w \qquad (V)$$

wherein $R^4$-BINAP is as defined above; Y represents $ClO_4$, $BF_4$, or $PF_6$; when e represents 0, then v represents 1, and w represents 2; and when e represents 1, then v represents 2, and w represents 1.

2. A process as claimed in claim 1, wherein said ruthenium-optically phosphine complex is represented by formula (III).

3. A process as claimed in claim 1, wherein said ruthenium-optically phosphine complex is represented by formula (V).

* * * * *